June 20, 1972 P. A. VOGEL Plant Pat. 3,218
CHRYSANTHEMUM PLANT
Filed Nov. 19, 1970
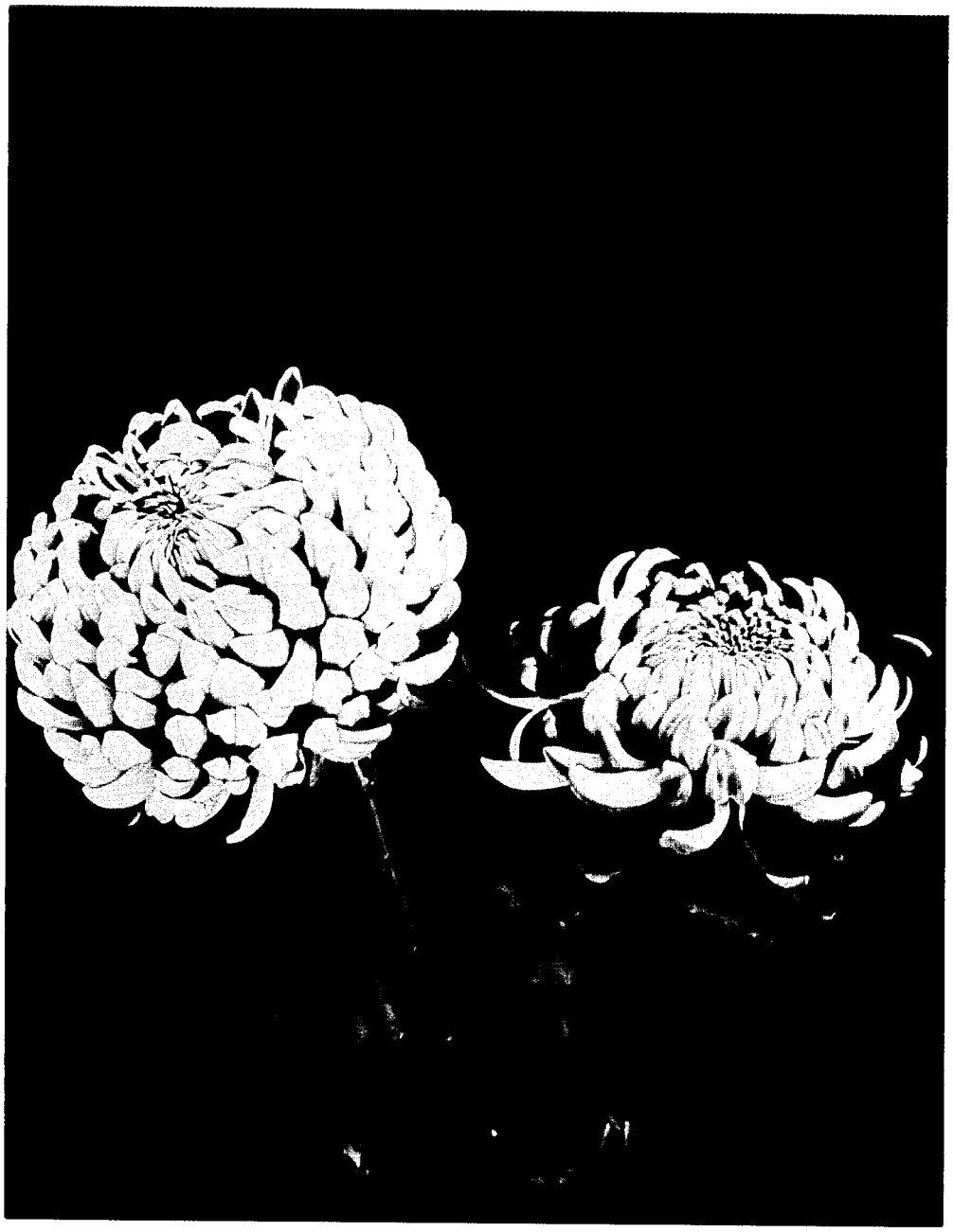
Inventor.
Paul A. Vogel
By: Robb & Robb
Attorneys.

United States Patent Office

Plant Pat. 3,218
Patented June 20, 1972

3,218
CHRYSANTHEMUM PLANT

Paul A. Vogel, Encinitas, Calif., assignor to Manatee, Incorporated, Encinitas, Calif.

Filed Nov. 19, 1970, Ser. No. 91,228
Int. Cl. A01h 5/00
U.S. Cl. Plt.—82 1 Claim The present invention relates to a new and distinct variety of chrysanthemum plant which was discovered by me as a cultivated sport of the variety known as "Mrs. Roy" (unpatented), said discovery having been made by me among the regular chrysanthemum plantings being grown by my assignee on its property located at Encinitas, Calif.

At the time of my discovery, many plants of the variety "Mrs. Roy" were being commercially grown under my direction and supervision. When the plants came into bloom during these growing operations at Encinitas, Calif., my attention was attracted to one particular plant which bore flowers of an unusual and distinctive color quite different from the flower color of all the other plants. On closer observation of that particular plant, I found that one of the plants of "Mrs. Roy" had sported, and I immediately took steps to carefully preserve the same and keep it under close observation. Shortly thereafter, I took cuttings therefrom and own-rooted the same in the greenhouse at Encinitas under normal greenhouse culture practice. These progeny and those resulting from subsequent asexual propagations have confirmed and convinced me, after prolonged tests and observations thereof, that this sport is definitely a new and distinct variety, as evidenced by the following unique combination of characteristics which are outstanding therein and which distinguish it from its parent variety "Mrs. Roy," as well as from all ther chrysanthemum varieties of which I am aware:

(1) A straight, upright, strong and free habit of growth;
(2) A large flower size;
(3) A distinctive and attractive flower color generally corresponding to near Chianti Antique Ruby on the inside of the petals and near Martius Yellow on the reverse side of the petals;
(4) Good hardiness to temperatures normally prevailing in southern latitudes, both outdoors and in the greenhouse; and
(5) A suitability for being forced into bloom at any time of year by appropriate control of light and temperature conditions applicable to standard 10-week chrysanthemum varieties.

Asexual reproduction of my new variety by own-rooted cuttings, as performed by me at Encinitas, Calif., shows that the foregoing characteristics and distinctions come true to form and are established and transmitted through succeeding propagations.

The accompanying drawing shows typical specimens of the vegetative growth and flowers of my new chrysanthemum variety in different stages of development and as depicted in color as nearly true as it is reasonably possible to make the same in an illustration of this character.

The following is a detailed description of the new variety, with color terminology in accordance with Ridgway's Color Standards and Nomenclature:

Parentage: Sport of "Mrs. Roy."
Classification: Incurved type.

Location where grown and observed: Encinitas, Calif.
Growth: Upright; straight; strong; free; average 4 feet tall when grown in greenhouse in southern latitudes; excellent both outdoors and in greenhouse.
Cold resistance: Comparable to "Mrs. Roy"; grows well year round in southern latitudes such as 33°.
Blooming period: At any time of year in southern latitudes.

*Flower*

Bud:
*Color.*—When sepals first divide—inside of petals—Dark Chianti Antique Ruby, Plate 6. Reverse of petals—Dark Martius Yellow, Plate 9. When petals begin to unfurl—inside of petals—Chianti Antique Ruby, Plate 6. Reverse of petals—Martius Yellow, Plate 9. When half-blown—inside of petals—Light Chianti Antique Ruby, Plate 6. Reverse of petals—Light Martius Yellow, Plate 9, with overtones of Chianti Antique Ruby, Plate 6 on the tips.
*Peduncle.*—Color—Light Cress Green, Plate 31. Strength—strong.

Bloom:
*Size.*—From 5 inches to 5¾ inches in diameter.
*Stem.*—Normal; strong.
*Form.*—Incurved.
*Petalage.*—Double.
*Color.*—Center of flower—Dark Martius Yellow, Plate 9, with overtones of Chianti Antique Ruby, Plate 6 at the tips. Outer petals—inside of petals—Light Chianti Antique Ruby, Plate 6. Reverse of petals—Light Martius Yellow, Plate 9, with overtones of Chianti Antique Ruby, Plate 6 on the tips. Base of petals—Light Lumiere Green, Plate 17.
*General color tonality.*—Inside of petals—uniform variations of Chianti Antique Ruby, Plate 6. Reverse of petals—uniform variations of Martius Martius Yellow, Plate 9.
*Petals.*—Texture—smooth; waxy. Form—oval.
*Fragrance.*—Typical chrysanthemum.

*Plant*

Foliage:
*Size.*—Medium.
*Quantity.*—Normal.
*Color.*—Upper side—Dark Cress Green, Plate 31. Reverse side—Bice Green, Plate 17.
*Texture.*—Leathery.

I claim:

1. A new and distinct variety of chrysanthemum plant of the incurved type, substantially as herein shown and described, characterized particularly as to novelty by the unique combination of a straight, upright, strong and free habit of growth, a large flower size, a distinctive and attractive flower color generally corresponding to near Chianti Antique Ruby on the inside of the petals and near Martius Yellow on the reverse side of the petals, good hardiness, both outdoors and in the greenhouse, and a suitablity for year around blooming in southern latitudes.

No references cited.

ROBERT E. BAGWILL, Primary Examiner